United States Patent
Marui (10) Patent No.: US 10,145,809 B2
(45) Date of Patent: Dec. 4, 2018

(54) X-RAY DIFFRACTION DEVICE AND SENSITIVITY CALIBRATION METHOD FOR X-RAY DIFFRACTION DEVICE

(71) Applicant: SHIMADZU CORPORATION, Kyoto-shi, Kyoto (JP)

(72) Inventor: Takao Marui, Sorakugun (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 193 days.

(21) Appl. No.: 15/195,246

(22) Filed: Jun. 28, 2016

(65) Prior Publication Data

US 2017/0371047 A1    Dec. 28, 2017

(51) Int. Cl.
G01N 23/207 (2018.01)
G01T 7/00 (2006.01)

(52) U.S. Cl.
CPC .......... G01N 23/207 (2013.01); G01T 7/005 (2013.01); *G01N 2223/303* (2013.01)

(58) Field of Classification Search
CPC .................. G01T 7/005; G01N 23/207; G01N 2223/303; G01N 23/2055
See application file for complete search history.

(56) References Cited

U.S. PATENT DOCUMENTS

| | | | | |
|---|---|---|---|---|
| 6,148,057 A | * | 11/2000 | Urchuk | A61B 6/583 378/18 |
| 2013/0108021 A1 | * | 5/2013 | Durst | G01N 23/207 378/71 |

FOREIGN PATENT DOCUMENTS

| | | |
|---|---|---|
| JP | H01-270651 A | 10/1989 |
| JP | 10-185844 A | 7/1998 |
| JP | 2002528216 A | 9/2002 |
| WO | 0025678 A1 | 5/2000 |
| WO | 2013/066843 A1 | 5/2013 |

OTHER PUBLICATIONS

Communication dated Sep. 12, 2017, from the Japanese Patent Office in counterpart application No. 2014-027374.
Communication dated Feb. 21, 2017, issued from the Japan Patent Office in counterpart Japanese Patent Application No. 2014-027374.

* cited by examiner

*Primary Examiner* — Glen Kao
(74) *Attorney, Agent, or Firm* — Sughrue Mion, PLLC

(57) ABSTRACT

The invention provides a sensitivity correction coefficient calculating system for an X-ray detector with which the sensitivity correction coefficient can be calculated using a multipurpose X-ray source instead of a specific X-ray source. In the sensitivity correction coefficient calculating system for an X-ray detector having a detection surface where detection elements for detection the X-ray intensity are aligned one-dimensionally or two-dimensionally, fitting is carried out on the measured X-ray intensity detected by a detection element using an approximation function so as to calculate the sensitivity correction coefficient using the calculated X-ray intensity calculated from the approximation function and the measured X-ray intensity.

6 Claims, 5 Drawing Sheets

Prior Art

X-RAY DIFFRACTION DEVICE AND SENSITIVITY CALIBRATION METHOD FOR X-RAY DIFFRACTION DEVICE

BACKGROUND OF THE INVENTION

1. Field of the Invention

The present invention relates to a sensitivity correction coefficient calculating system for an x-ray detector that is used for X-ray analyzers such as X-ray diffraction analyzers, X-ray fluorescence analyzers and X-ray absorption spectroscopes, and in particular to an X-ray diffraction analyzer for qualitatively and quantitatively analyzing sample components by detecting X-rays diffracted by a sample when irradiating the sample with characteristic X-rays.

2. Description of Related Art

In X-ray diffraction analyzers, a powder sample is irradiated with characteristic X-rays from an X-ray source so as to detect the diffracted X-rays that are emitted from the powder sample for each diffraction angle by means of an X-ray detector mounted in a goniometer (see Patent Document 1). As a result, crystal components included in the powder sample are qualitatively and quantitatively analyzed.

Figure 8:
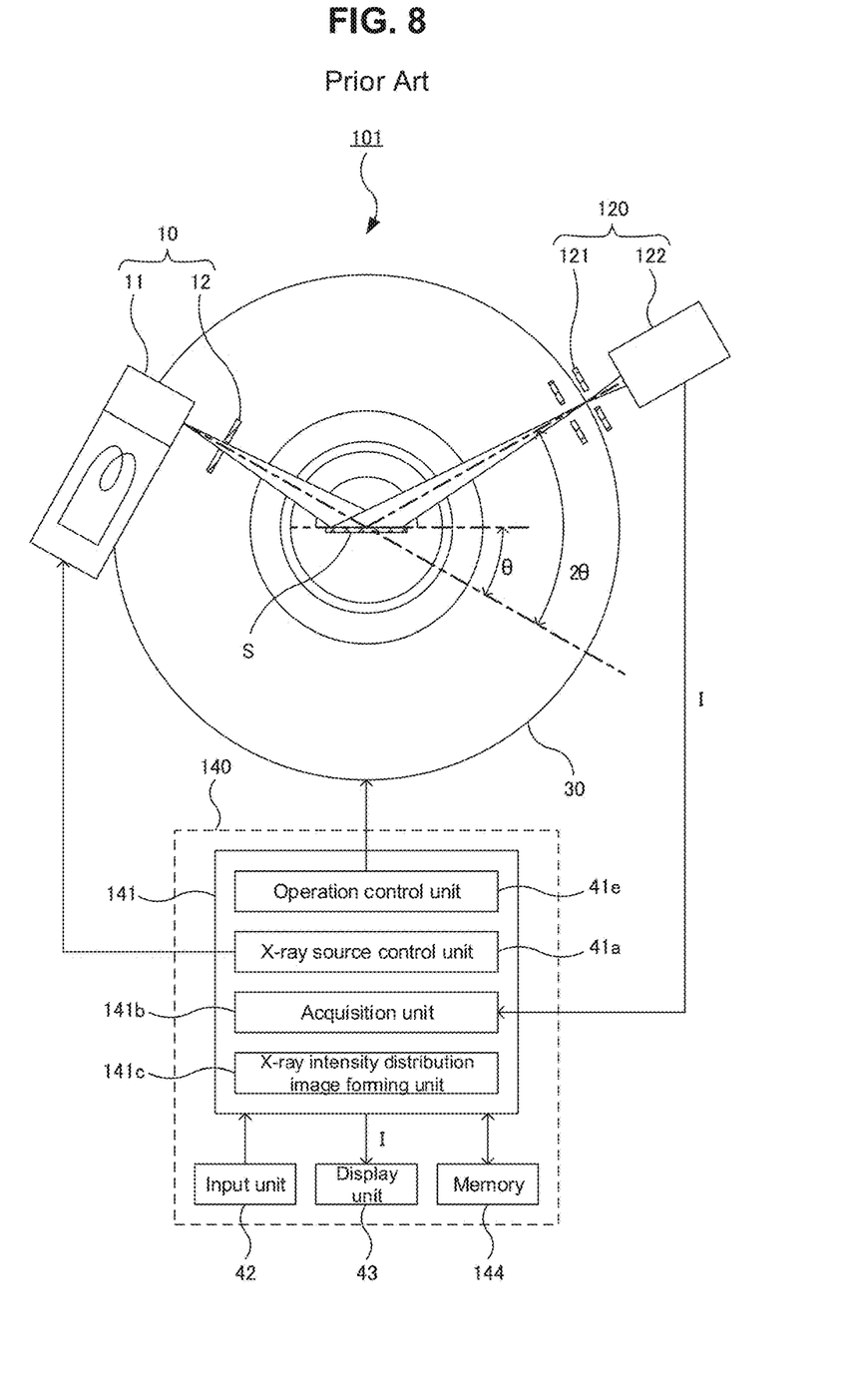
FIG. 8 is a schematic diagram showing the configuration of an example of a conventional X-ray diffraction analyzer.

FIG. 8 is a schematic diagram showing the configuration of an example of a conventional X-ray diffraction analyzer. An X-ray diffraction analyzer 101 is provided with an X-ray source unit 10, a detection unit 120, a goniometer 30 and a computer 140 for controlling the entirety of the X-ray diffraction analyzer 101. Here, a sample S is a powder sample that is formed in a square plate shape having sides of approximately 20 mm by means of a sample holder.

The X-ray source unit 10 is provided with an X-ray tube 11 and an emanation slit 12 installed in a predetermined location and having a predetermined slit width. The X-ray tube 11 is a point focus type X-ray bulb having a housing inside of which a target, which is an anode, and a filament, which is a cathode, are placed. As a result, thermal electrons emitted from the filament collide with the target when a high voltage is applied between the target and the filament so that characteristic X-rays generated in the target can be emitted. In addition, the characteristic X-rays are emitted with their spread being regulated to approximately 1 degree to 3 degrees by means of the emanation slit 12.

The detection unit 120 is provided with a detection slit 121 and an X-ray detector 122 made of one (1ch) detection element. In addition, the measured X-ray intensity (read out data) I is outputted to the computer 140 from the detection element.

Furthermore, the detection unit 120 is mounted along the 2θ axis of the goniometer 30, and at the same time, the powder sample S is mounted along the θ axis of the goniometer 30. When the detection unit 120 and the powder sample S are rotated around the center axis of the goniometer 30 in accordance with a θ-2θ interlocking drive method, the measured X-ray intensity I is outputted for each diffraction angle so that an X-ray diffraction pattern can be gained.

The computer 140 is provide with a CPU 141, an input unit 42, a display unit 43 and a memory 144. The functions processed by the CPU 141 are described in the boxes, which include an X-ray source control unit 41a for allowing the X-ray tube 11 to emit characteristic X-rays, an acquisition unit 141b for acquiring the measured X-ray intensity I from the X-ray detector 122, an X-ray intensity distribution image forming unit 141c for forming an X-ray intensity distribution image, and an operation control unit 41e for driving and rotating the goniometer 30.

In the X-ray diffraction analyzer 101, the user (client) first mounts a powder sample S at the center of the goniometer 30 along the θ axis in order to analyze the powder sample S. Then, the surface of the powder sample S is irradiated with characteristic X-rays emitted from the X-ray tube 11 via the emanation slit 12. At this time, the powder sample S and the X-ray detector 122 are driven and rotated while being interlocked in such a manner that the 2θ axis and the θ axis of the goniometer 30 keep the relationship of 2θ being two times as large as θ, and thus, the diffracted X-rays emitted from the powder sample S are detected by the detection slit 121 and the X-ray detector 122 that are mounted along the 2θ axis.

In addition, an X-ray diffraction analyzer has been developed that is provided with a line sensor having a detection surface where N (1280, for example) detection elements for detecting the X-ray intensity are aligned one-dimensionally as the detection unit in order to analyze the powder sample S for a short period of time.

Figure 6:
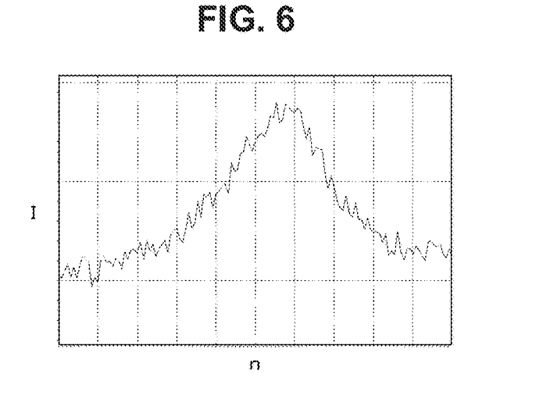
FIG. 6 is a graph showing the measured X-ray intensity distribution of a powder sample detected by a line sensor.

Incidentally, the measured X-ray intensity data outputted by the line sensor includes inconsistency in the intensity instead of providing a true (precise) X-ray intensity distribution due to the inconsistency in the sensitivity characteristics from among the detection elements (see FIG. 6).

Figure 7:
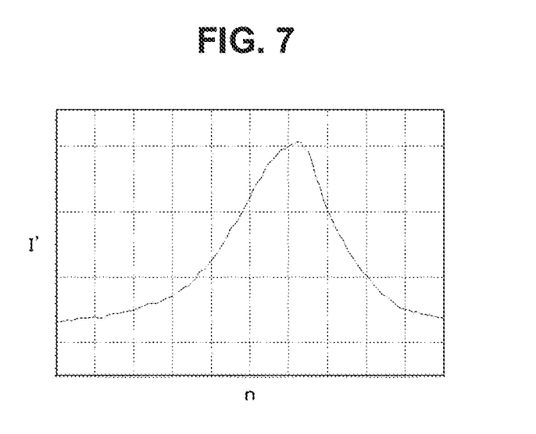
FIG. 7 is a graph showing a corrected X-ray intensity distribution image.

Therefore, X-ray diffraction analyzers with a line sensor have their memories store a sensitivity correction coefficient $\alpha_n$ (detection element number n=1, 2, ..., N) for each detection element in advance. When the user measures the powder sample S, the CPU (X-ray intensity distribution image forming unit) carries out a correction operation on the measured X-ray intensity (read out data) $I_n$ detected by each detection element using the sensitivity correction coefficient $\alpha_n$ and the following formula (1) so as to form a corrected X-ray intensity distribution image that shows the relationship between the corrected X-ray intensity $I_n'$ and the detection element number n, which is then displayed on the display unit (see FIG. 7).

corrected X-ray intensity (measured data)
$I_n'$=measured X-ray intensity $In$×sensitivity correction coefficient $\alpha_n$  (1)

Here, the sensitivity correction coefficient $\alpha_n$ (detection element number n=1, 2, ..., N) stored in the memory is calculated using the average X-ray intensity $I_{ave}$ of the measured X-ray intensity $I_n$, detected for all the detection elements by irradiating the entire surface of the detector with X-rays of a uniform intensity, the measured X-ray intensity In for each detection element and the following formula (2).

sensitivity correction coefficient $\alpha_n$=average X-ray intensity $I_{ave}$/measured X-ray intensity $I_n$  (2)

where $I_{ave}=(I_1+I_2+ \ldots +I_n+ \ldots +I_{(N-1)}+I_N)/N$

PRIOR ART DOCUMENT

Patent Document

Patent Document 1: Japanese Unexamined Patent Publication H10 (1998)-185844

SUMMARY OF THE INVENTION

1. Problem to be Solved by the Invention

In accordance with the above-described sensitivity correction coefficient calculating method, it is necessary to prepare a uniform X-ray source (specific X-ray source) that is large scale and expensive. Though such a uniform X-ray source can be deployed in line sensor production factories, it is difficult to deploy such a uniform X-ray source in fields where users use the system. Therefore, such a problem arises that it is necessary to disengage the line sensor and send it back to the line sensor production factory in the case where it becomes necessary to readjust the sensitivity correction coefficient $\alpha_n$ in a field where a user uses the system. Another problem arises such that it is difficult to confirm whether or not it is necessary to readjust the sensitivity correction coefficient $\alpha_n$ when the user is using the X-ray diffraction analyzer.

Therefore, an object of the present invention is to provide a sensitivity correction coefficient calculating system for an X-ray detector with which the sensitivity correction coefficient $\alpha_n$ can be calculated using a multipurpose X-ray source that can be easily prepared instead of a uniform X-ray source (specific X-ray source). Another object of the invention is to provide an X-ray diffraction analyzer where readjustment of the sensitivity correction coefficient $\alpha_n$ is possible.

2. Means for Solving Problem

In order to achieve the above-described objects, the sensitivity correction coefficient calculating system for an X-ray detector according to the present invention is a sensitivity correction coefficient calculating system for an X-ray detector having a detection surface where detection elements for detecting an X-ray intensity are aligned one-dimensionally or two-dimensionally, wherein an X-ray source, where fitting of the X-ray intensity distribution is possible with an approximation function for the X-rays with which the above-described detection surface is irradiated, is used to carry out function fitting on the measured X-ray intensity detected for each detection element, and the sensitivity correction coefficient for each detection element is found from the ratio of the calculated X-ray intensity calculated from the fitted approximation function to the measured X-ray intensity.

In the sensitivity correction coefficient calculating system for an X-ray detector according to the present invention, the user or a service person first carries out measurement under the conditions where the detector is irradiated with X-rays having no steep differences in the intensity. That is to say, measurement is carried out with the apparatus available to the user instead of preparing a specific X-ray source. Next, the user or the service person carries out fitting on the thus-measured X-ray intensity distribution using an approximation function. After that, the sensitivity correction coefficient $\alpha_n$ is calculated for each detection element using the measured X-ray intensity $I_n$ detected for each detection element, the calculated X-ray intensity $i_n$ calculated from the approximation function and the following formula (3).

sensitivity correction coefficient $\alpha_n$=calculated X-ray intensity $i_n$/measured X-ray intensity $I_n$     (3)

3. Effects of the Invention

As described above, in the sensitivity correction coefficient calculation system for an X-ray detector according to the present invention, the sensitivity correction coefficient $\alpha_n$ can be calculated as long as the detector can be irradiated with X-rays without steep differences in the intensity depending on the location even without preparing a specific X-ray source.

In addition, the invention may be implemented using an X-ray source where fitting is possible for the intensity distribution using a certain approximation function in a line sensor production factory or the like. In this case, a multipurpose X-ray source can be used as the X-ray source prepared in the line sensor production factory or the like.

Other Means for Solving Problem and Effects Thereof

According to another aspect of the invention, the above-described approximation function is a polynomial function.

According to still another aspect of the invention, the above-described approximation function is the sum of a polynomial function and a Gaussian function.

The X-ray analyzer according to the present invention is provided with: an X-ray source for emitting characteristic X-rays to a sample; an X-ray detector having a detection surface where detection elements for detecting the intensity of the X-rays emitted from the above-described sample are aligned one-dimensionally or two-dimensionally; a correction coefficient storage unit for storing the sensitivity correction coefficient for each detection element; and an X-ray intensity distribution image forming unit for forming a corrected X-ray intensity distribution image by carrying out correction operations on the measured X-ray intensities detected by the above-described detection elements using the above-described sensitivity correction coefficients, and is further provided with: a control unit for carrying out function fitting on the measured X-ray intensity distribution gained by measuring an already-known sample and allowing the correction coefficient storage unit to store the ratio of the calculated X-ray intensity calculated by the fitting function to the measured X-ray intensity as the sensitivity correction coefficient for each detection element.

In the X-ray analyzer according to the present invention, the user or a service person first sets the system to a correction coefficient calculating mode. That is to say, a sample analyzing mode with which the corrected X-ray intensity $I_n'$ is to be calculated is turned off. Next, the user or the service person places a reference sample (sample that emits X-rays having a region without a steep difference in the intensity) S'. That is to say, the sensitivity correction coefficient $\alpha_n$ is calculated when using the X-ray analyzer.

Next, the user or the service person allows the detection surface to be irradiated with the X-rays from the thus-prepared reference sample S'. After that, the user or the service person carries out fitting on the intensity distribution of the X-rays emitted from the thus-prepared reference sample S' using an approximation function (cubic function, for example). Then, the sensitivity correction coefficient $\alpha_n$ for each detection element is calculated using the measured X-ray intensity $I_n$ detected for each detection element, the calculated X-ray intensity $i_n$ calculated from the approximation function, and the formula (3). Finally, the N sensitivity correction coefficients $\alpha_n$ are stored in the correction coefficient storage unit.

As described above, in the X-ray analyzer according to the present invention, the sensitivity correction coefficient $\alpha_n$ can be calculated simply by placing a reference sample (sample that emits X-rays having a region without a steep difference in the intensity depending on the location) S' after turning the system to an appropriate mode, for example, the correction coefficient calculating mode, not only before the X-ray analyzer is shipped to the user, but also after being shipped.

In addition, according to another aspect of the invention, the above-described control unit uses a multinomial function as the above-described fitting function and uses a background region where there are no peaks when the above-described already-known sample is measured.

Furthermore, according to still another aspect of the invention, the above-described control unit uses the sum of a multinomial function and a Gaussian function as the above-described fitting function and carries out fitting so that the Gaussian function is added to the location of a peak in the measured X-ray intensity distribution of the above-described already-known sample.

DETAILED DESCRIPTION OF EMBODIMENTS

In the following, the embodiments of the present invention are described in reference to the drawings. The present invention is not limited to the below-described embodiments, but needless to say, includes various modifications as long as the gist of the present invention is not deviated from.

Figure 1:
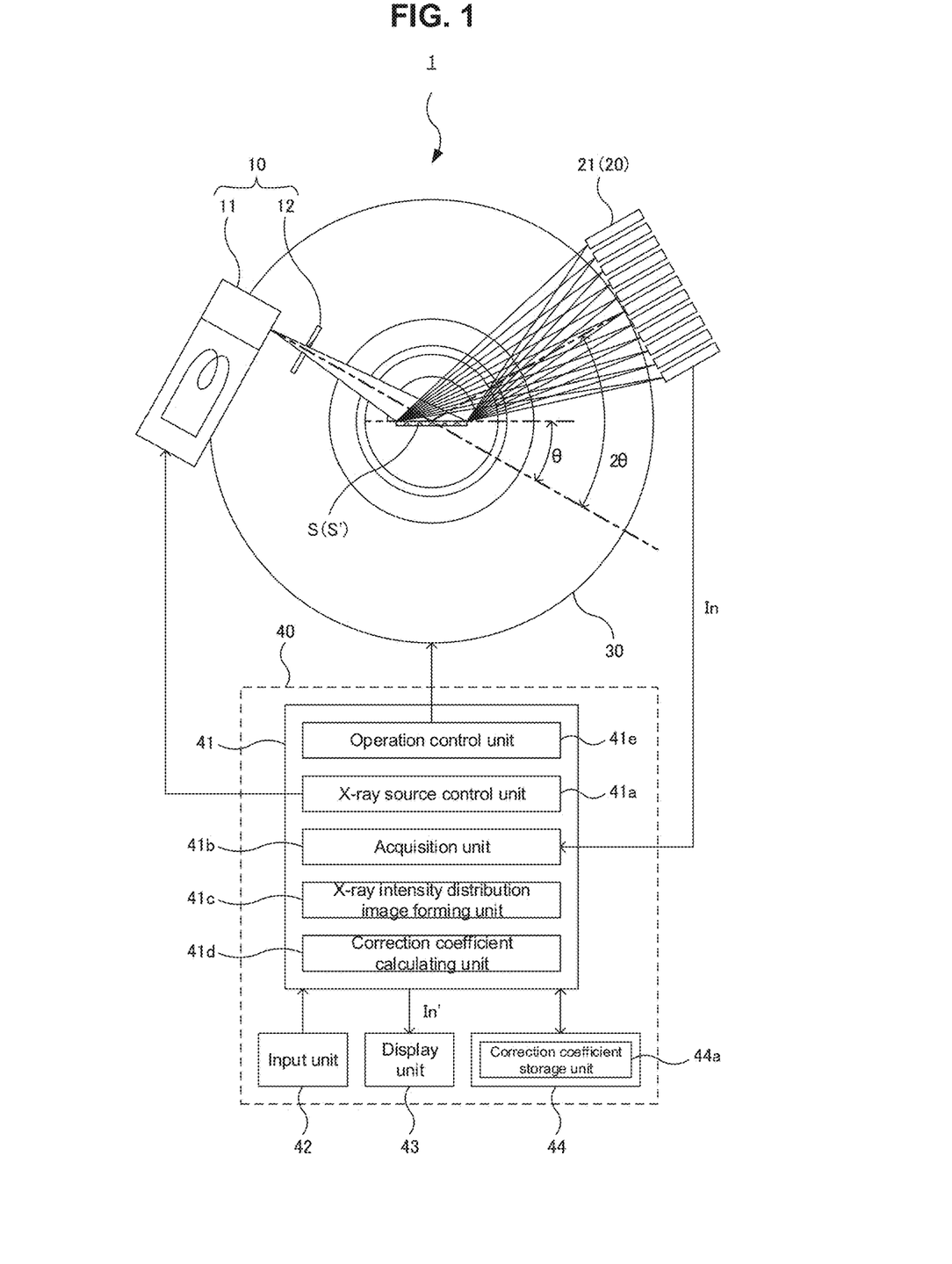
FIG. 1 is a schematic diagram showing the configuration of an example of the X-ray diffraction analyzer according to one embodiment of the present invention.

FIG. 1 is a schematic diagram showing the configuration of one example of the X-ray diffraction analyzer according to one embodiment of the present invention. Here, the same symbols are attached to the corresponding components as in the X-ray diffraction analyzer 101.

An X-ray diffraction analyzer 1 is provided with an X-ray source unit 10, a detection unit 20, a goniometer 30 and a computer 40 for controlling the entirety of the X-ray diffraction analyzer 1.

The detection unit 20 is provided with a line sensor (X-ray detector) 21 having a detection surface where N (1280, for example) detection elements (semiconductor elements) are aligned one-dimensionally. Thus, the measured X-ray intensity (read out data) $I_n$ (detection element number n=1, 2 . . . , N) can be outputted to the computer (control unit) 40 from each detection element.

In addition, the detection unit 20 is mounted along the 2θ axis of the goniometer 30, and at the same time, the sample S to be measured is mounted along the θ axis of the goniometer 30. The detection unit 20 and the sample S are rotated around the center axis of the goniometer 30 in accordance with the θ-2θ interlocking drive method.

The computer 40 is provided with a CPU 41, an input unit 42, a display unit 43 and a memory 44. The functions processed by the CPU 41 are described in the boxes, which include an X-ray source control unit 41a for allowing the X-ray tube 11 to emit characteristic X-rays, an acquisition unit 41b for acquiring the N measured X-ray intensities In from the line sensor 21, an X-ray intensity distribution image forming unit 41c for forming a corrected X-ray intensity distribution image, a corrected coefficient calculating unit 41d for calculating the N sensitivity correction coefficients $\alpha_n$, and an operation control unit 41e for driving and rotating the goniometer 30.

In addition, the memory 44 has a corrected coefficient storage unit 44a for storing the N sensitivity correction coefficients $\alpha_n$.

When the sample analyzing mode is turned on due to the input signal from the input unit 42, the X-ray intensity distribution image forming unit 41c substitutes the sensitivity correction coefficient $\alpha_n$ stored in the corrected coefficient storage unit 44a and the measured X-ray intensity $I_n$ acquired by the acquisition unit 41b into the formula (1) so as to calculate the corrected X-ray intensity $I_n'$, and forms a corrected X-ray intensity distribution image that shows the relationship between the corrected X-ray intensity $I_n'$ and the detection element number n so as to display the resulting image on the display unit 43 in accordance with the control.

When the user turns on the sample analysis mode, the sample S to be measured is mounted at the center of the goniometer 30 along the θ axis, and a powder sample that is formed in a square plate shape having sides of approximately 20 mm by means of a sample holder can be cited as an example of the sample S to be measured.

When the sample analyzing mode is turned off due to the input signal from the input unit 42, that is to say, when the system is set to the correction coefficient calculating mode, the correction coefficient calculating unit 41d finds an approximation cubic function (4') by carrying out fitting on the measured X-ray intensity In acquired by the acquisition unit 41b using the cubic function (4) for each detection element and substitutes the calculated X-ray intensity in calculated from the approximation cubic function (4') and the measured X-ray intensity In into the formula (3) so as to calculate the sensitivity correction coefficient $\alpha_n$, and thus allows the correction coefficient storage unit 44a to store the resulting sensitivity correction coefficient $\alpha_n$ in accordance with the control.

$$I = an^3 + bn^2 + cn + d \quad (4)$$

$$I = -1^{-0.6}n^3 - 0.0024n^2 + 0.384n + 31744 \quad (4')$$

When the user or a service person sets the system to the correction coefficient calculating mode, a reference sample (already-known sample) S' that emits X-rays having a region without a steep difference in the intensity is mounted at the center of the goniometer 30 along the θ axis, and a square copper plate having sides of approximately 20 mm can be cited as an example of the reference sample S'. When the acquisition unit 41b acquires the measured X-ray intensity In from the reference sample S' which is a copper plate that emits X-rays having a region (background region) where there are no diffraction peaks, the operation control unit 41e may automatically drive and rotate the goniometer 30 so that the detection surface of the line sensor 21 can be irradiated with the diffracted X-rays from the region where there are no diffraction peaks.

Figure 2:
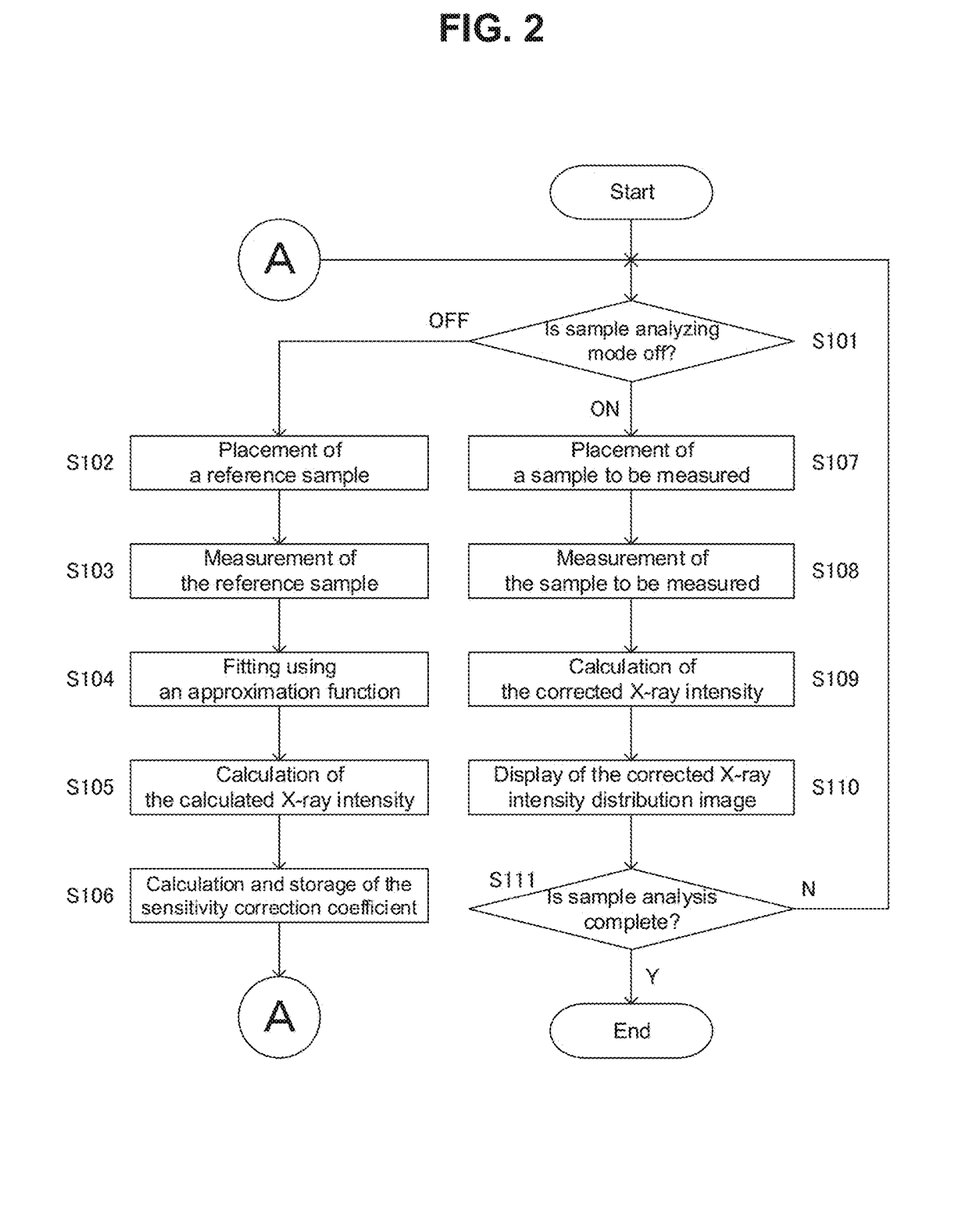
FIG. 2 is a flow chart showing the method for using the X-ray diffraction analyzer according to the present invention.

Next, an example of a method for using the X-ray diffraction analyzer 1 is described. FIG. 2 is a flow chart showing the method for use.

First, in the process in step S101, the CPU 41 determines whether or not the sample analyzing mode has been turned off.

When it is determined that the sample analyzing mode has been turned off, that is to say, the system has been set to the correction coefficient calculating mode, the procedure moves to the process in step S102.

In the process in step S102, the user places a reference sample S' at the center of the goniometer 30 along the θ axis.

Figure 3:
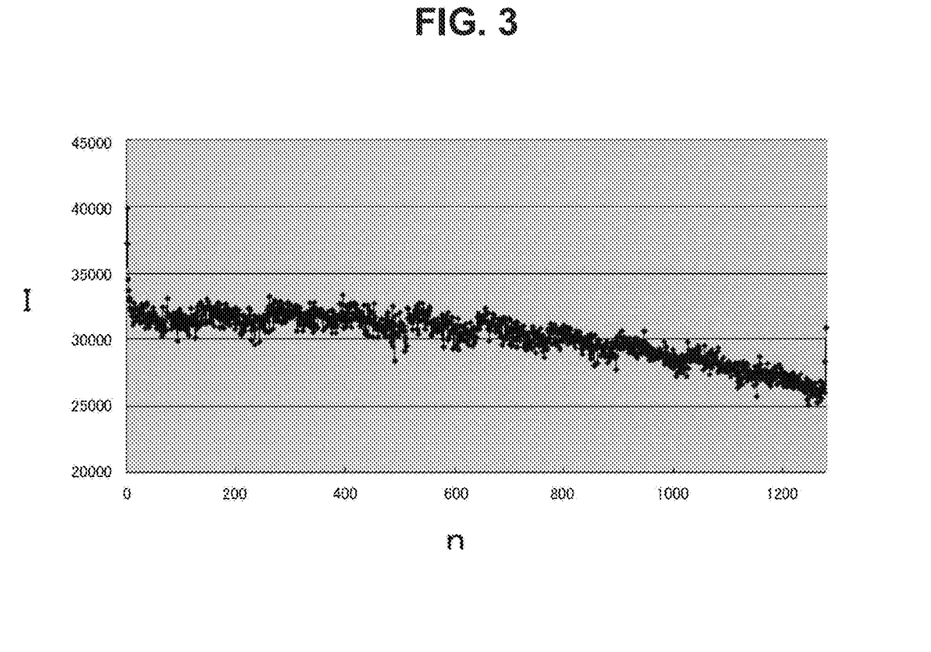
FIG. 3 is a graph showing the measured X-ray intensity distribution of a reference sample detected by a line sensor.

Next, in the process in step S103, the surface of the reference sample S' is irradiated with the characteristic X-rays emitted from the X-ray tube 11 via the emanation slit 12, and the line sensor 21 that is mounted along the 2θ axis, detects the diffracted X-rays emitted from the reference sample S'. FIG. 3 is a graph showing the intensity distribution of the measured X-rays from the reference sample S' that are detected by the line sensor 21.

Next, in the process in step S104, the correction coefficient calculating unit 41d carries out fitting on the measured X-ray intensity $I_n$ acquired by the acquisition unit 41b with the cubic function (4) using a publicly-known operation, and thus prepares an approximation cubic function (4').

Figure 4:
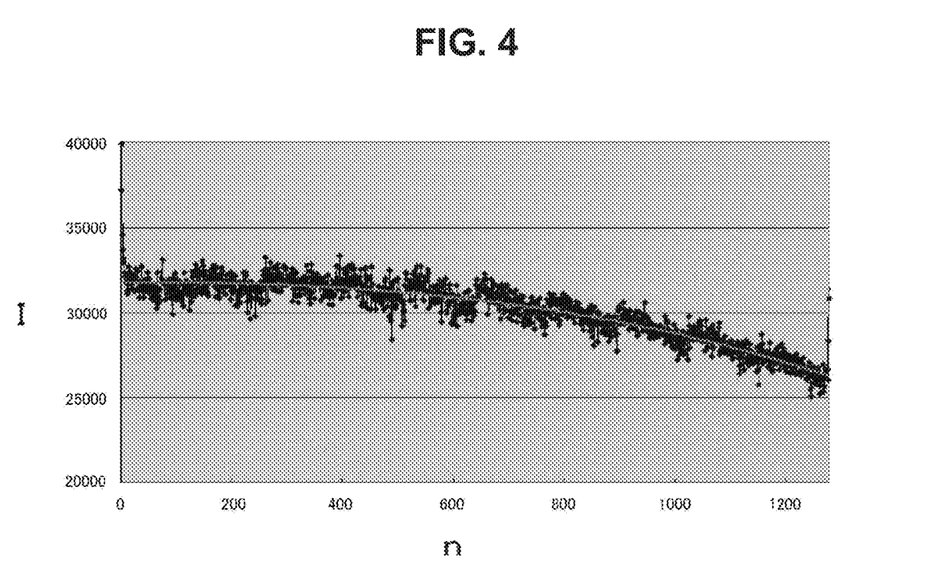
FIG. 4 is a graph showing the overlapping of the measured X-ray intensities $I_n$ for the respective detection elements and the calculated X-ray intensity $i_n$.

Furthermore, in the process in step S105, the approximation cubic function (4') is used to calculate the calculated X-ray intensity $i_n$ for each detection element using the approximation cubic function (4'). FIG. 4 is a graph showing the overlapping of the measured X-ray intensities $I_n$ for the respective detection elements and the calculated X-ray intensity $i_n$.

Figure 5:
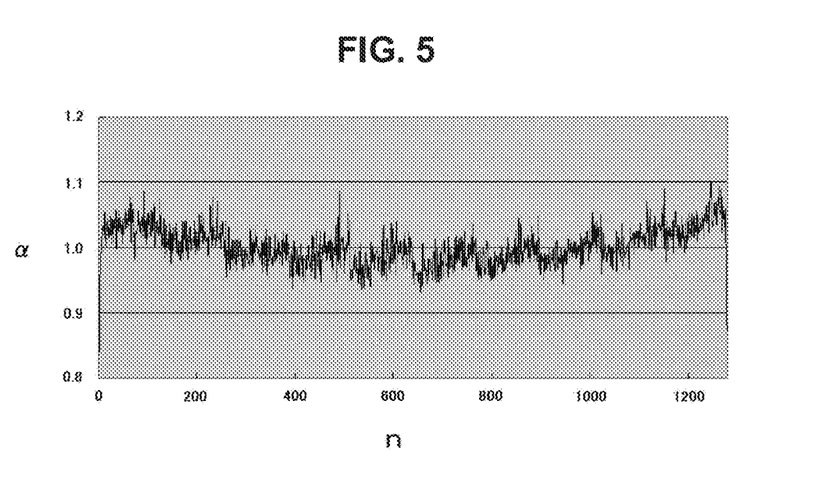
FIG. 5 is a graph showing the sensitivity correction coefficients for the respective detection elements.

Next, in the process in step S106, the correction coefficient calculating unit 41d substitutes the measured X-ray intensity $I_n$ for each detection element and the calculated X-ray intensity $i_n$ into the formula (3) so as to calculate the sensitivity correction coefficient $\alpha_n$ for each detection element, and stores the resulting sensitivity correction coefficient $\alpha_n$ the correction coefficient storage unit 44a. FIG. 5 is a graph showing the sensitivity correction coefficients $\alpha_n$ for the respective detection elements. Then, the procedure returns to the process in step S101 after the completion of the process in step S106. That is to say, when the correction coefficient calculating mode is set, the processes in steps S102 through S106 are carried out so that the N sensitivity correction coefficients $\alpha_n$ stored in the correction coefficient storage unit 44a are updated to N new values.

Meanwhile, when it is determined that the sample analyzing mode has been turned on in the process in step S101, the user places a sample S to be measured at the center of the goniometer 30 along the θ axis in the process in step S107.

Next, in the process in step S108, the surface of the sample S to be measured is irradiated with the characteristic X-rays emitted from the X-ray tube 11 via the emanation slit 12, and the line sensor 21 that is mounted along the 2θ axis detects the diffracted X-rays emitted from the sample S to be measured. FIG. 6 is a graph showing the intensity distribution of the measured X-rays from the sample S to be measured detected by the line sensor 21.

Next, in the process in step S109, the X-ray intensity distribution image forming unit 41c substitutes the sensitivity correction coefficient $\alpha_n$ stored in the correction coefficient storage unit 44a and the measured X-ray intensity $I_n$ acquired by the acquisition unit 41b into the formula (1) so as to calculate the corrected X-ray intensity $I_n'$.

Next, in the process in step S110, the X-ray intensity distribution image forming unit 41c forms a corrected X-ray intensity distribution image showing the relationship between the corrected X-ray intensity $I_n'$ and the detection element number n and displays the resulting image on the display unit 43. FIG. 7 is a graph showing the corrected X-ray intensity distribution image.

Next, in the process in step S111, it is determined whether or not a new sample S to be measured is to be analyzed. When it is determined that a new sample S to be measured is to be analyzed, the procedure returns to the process instep S101. When it is determined that a new sample S to be measured is not to be analyzed, the present flow chart is complete.

As described above, in the X-ray diffraction analyzer 1 according to the present invention, the simple operations of setting the correction coefficient calculating mode at an appropriate time after shipping to the user and placing a reference sample S' can allow the sensitivity correction coefficient $\alpha_n$ to be calculated.

Other Embodiments (1) Though the X-ray diffraction analyzer 1 has such a structure where a line sensor 21 having a detection surface where N detection elements are aligned one-dimensionally is provided and a one-dimensional approximation function (curve) is used as described above, the structure may be provided with an X-ray detector having a detection surface where N×M detection elements are aligned two-dimensionally where a two-dimensional approximation function (curved surface) is used.

(2) Though the X-ray diffraction analyzer 1 has such a structure where a cubic function (4) is used as an approximation function as described above, the structure may use a linear function or a quadratic function as an approximation function depending on the type of reference sample S'. Alternatively, the structure may use a combination of a cubic function and a Gaussian function as an approximation function. That is to say, the characteristics of the intensity distribution of the X-rays with which the detection surface is irradiated may be taken into consideration so that a function that is appropriate for these can be used.

(3) Though the above-described embodiment provides the structure of the X-ray diffraction analyzer 1, a structure of an X-ray fluorescence analyzer or an X-ray absorption spectroscope may be provided instead of the X-ray diffraction analyzer.

Though the sensitivity correction coefficient $\alpha_n$ is calculated when the X-ray detector is in the form of the X-ray diffraction analyzer 1, the sensitivity correction coefficient may be calculated by using a multipurpose X-ray source when the X-ray detector is in the form of a line sensor in a line sensor production factory, for example.

INDUSTRIAL APPLICABILITY

The present invention can be applied to X-ray analyzers that are used as X-ray diffraction analyzers, X-ray fluorescence analyzers and X-ray absorption spectroscopes.

EXPLANATION OF SYMBOLS

1 X-ray diffraction analyzer

21 Line sensor (X-ray detector)

What is claimed is:

1. An X-ray analyzer, comprising:
    an X-ray source for emitting characteristic X-rays to a sample;
    an X-ray detector having a detection surface where detection elements for detecting the intensity of the X-rays emitted from said sample are aligned one-dimensionally or two-dimensionally;
    a correction coefficient storage unit for storing a sensitivity correction coefficient for each detection element; and
    an X-ray intensity distribution image forming unit for forming a corrected X-ray intensity distribution image by carrying out correction operations on the measured X-ray intensities detected by said detection elements using said sensitivity correction coefficients, characterized by further comprising:
    a control unit for carrying out function fitting on the measured X-ray intensity distribution gained by measuring an already-known sample and allowing the correction coefficient storage unit to store the ratio of a calculated X-ray intensity calculated by the fitting function to the measured X-ray intensity as the sensitivity correction coefficient for each detection element.

2. The X-ray analyzer according to claim 1, characterized in that said control unit uses said fitting function as a polynomial function and uses a background region where there are no peaks when measuring said already-known sample.

3. The X-ray analyzer according to claim 1, characterized in that said control unit uses the sum of a polynomial function and a Gaussian function as said fitting function and carries out fitting so that the Gaussian function is added to the location of a peak in the measured X-ray intensity distribution of said already-known sample.

4. X-ray diffraction device comprising:
    an X-ray source using an X-ray tube that fires characteristic X-rays onto a sample, placed on an θ axis of a goniometer,
    an X-ray detector, placed on an 2θ axis of the goniometer, that has a detection surface comprising a plurality of detection elements that detect the strength of X-rays emitted from the sample, wherein the plurality of detection elements are arrayed either one-dimensionally or two-dimensionally;
    a calibration coefficient storage component for the storage of a sensitivity calibration coefficient for each of the plurality of detecting elements of the X-ray detector;
    an X-ray strength distribution image creation component that creates a calibrated X-ray strength distribution image by calibrating the measured X-ray strength detected by the plurality of detection elements using the aforesaid sensitivity calibration coefficient; and
    a control component that measures an X-ray-emitting standard sample having an area that does not contain a diffraction peak, uses an approximation function to perform function fitting of the measured X-ray strength distribution found by means of the measured X-ray strength detected by each of the plurality of detecting elements, and stores in the calibration coefficient storage component the ratio of the calculated X-ray strength calculated by means of this fitting function to the measured X-ray strength in the form of a sensitivity calibration coefficient for each of the plurality of detecting elements.

5. The X-ray diffraction device set forth in claim 4 wherein the control component uses a polynomial function for the fitting function.

6. A sensitivity calibration method for an X-ray diffraction device, the X-ray diffraction device comprising: an X-ray source using an X-ray tube that fires characteristic X-rays onto a sample placed on an θ axis of a goniometer; an X-ray detector placed on an 2θ axis of the goniometer that has a detection surface wherein a plurality of detection elements that detect the strength of X-rays emitted from the sample are arrayed either one-dimensionally or two-dimensionally; a calibration coefficient storage component for the storage of a sensitivity calibration coefficient for each detecting element of the X-ray detector; and an X-ray strength distribution image creation component that creates a calibrated X-ray strength distribution image by calibrating the measured X-ray strength detected by the plurality of detection elements using the sensitivity calibration coefficient, the sensitivity calibration method comprising:
    measuring a standard sample that emits X-rays having an area that does not contain a diffraction peak;
    using an approximation function to perform function fitting of a measured X-ray strength distribution found by means of the measured X-ray strength detected by each of the plurality of detecting elements; and
    storing in the calibration coefficient storage component the ratio of the calculated X-ray strength calculated by means of this fitting function to the measured X-ray strength in the form of a sensitivity calibration coefficient for each of the plurality of detecting elements.

* * * * *